United States Patent [19]
Beckenstein

[11] Patent Number: 5,569,237
[45] Date of Patent: Oct. 29, 1996

[54] MARKING DEVICE FOR BREAST SURGERY

[76] Inventor: Michael S. Beckenstein, 1113 Windridge Dr., Atlanta, Ga. 30350

[21] Appl. No.: 429,903

[22] Filed: Apr. 27, 1995

[51] Int. Cl.$^6$ ..................................................... A61B 17/00
[52] U.S. Cl. ............................ 606/1; 606/116; 606/186; 604/116
[58] Field of Search ............................ 606/1, 116, 186; 128/310, 305, 316; 33/297, 670, 671; 604/116; 401/256

[56] References Cited

U.S. PATENT DOCUMENTS

| | | |
|---|---|---|
| 3,502,070 | 3/1970 | Bliss . |
| 3,950,106 | 4/1976 | Braun ..................................... 401/256 |
| 4,576,163 | 3/1986 | Bliss . |
| 4,705,035 | 11/1987 | Givens ..................................... 128/316 |
| 4,838,854 | 6/1989 | Kuzmanovich . |
| 4,880,017 | 11/1989 | Soll et al. ............................... 128/316 |
| 4,892,096 | 1/1990 | Narayanan et al. ........................ 606/1 |
| 5,192,270 | 3/1993 | Carswell, Jr. . |

*Primary Examiner*—Michael Powell Buiz
*Assistant Examiner*—Kevin Truong
*Attorney, Agent, or Firm*—Pearne, Gordon, McCoy & Granger

[57] ABSTRACT

A breast marking device includes an annular body and a circular felt marking pad disposed on a front end of body which holds ink. A removable annular cap covers the felt marking pad and is secured to the body. The cap has a pair of annular walls which frictionally engage the body to removably secure the cap to the body. A projection extends from a front face of the cap which defines a circular, pointed, marking edge substantially concentric with the felt marking pad. The marking edge has substantially the same diameter as the felt marking pad. A stop is provided on the body to limit movement of the cap on the body such that the cap engages the stop to space the cap from the felt marking pad. A circular imprint is made on the breast with the marking edge so as to discolor flesh thereof. Once an imprint is made, a circle of ink is stamped with the felt marking pad substantially where the circular imprint was made. Before stamping the circle of ink, the location of the circular imprint is examined to determine whether the location of the circular imprint is accurate. If the location is not accurate, than the circular imprint is rubbed to reduce the discoloration and another circular imprint is made prior to stamping the circle of ink.

18 Claims, 2 Drawing Sheets

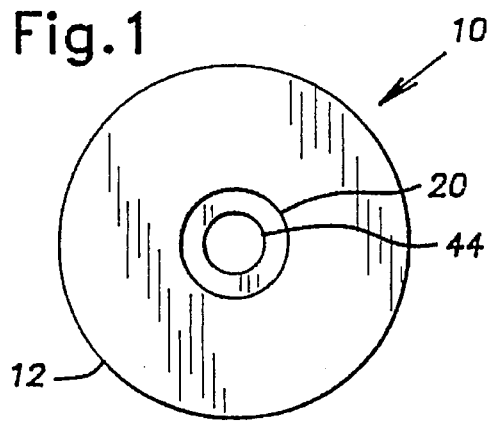
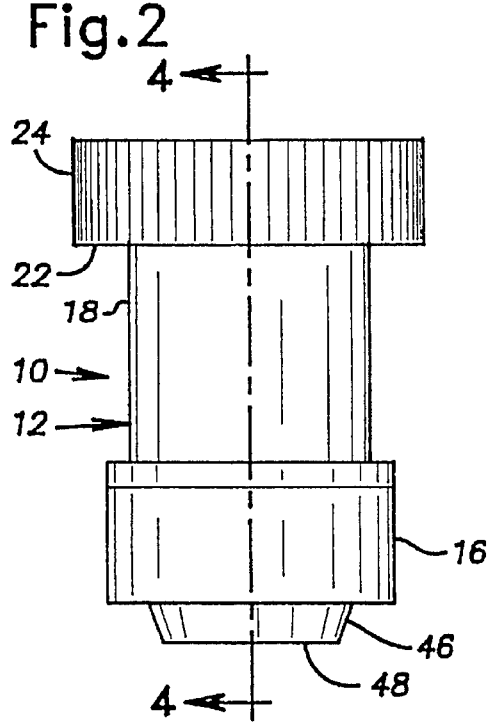
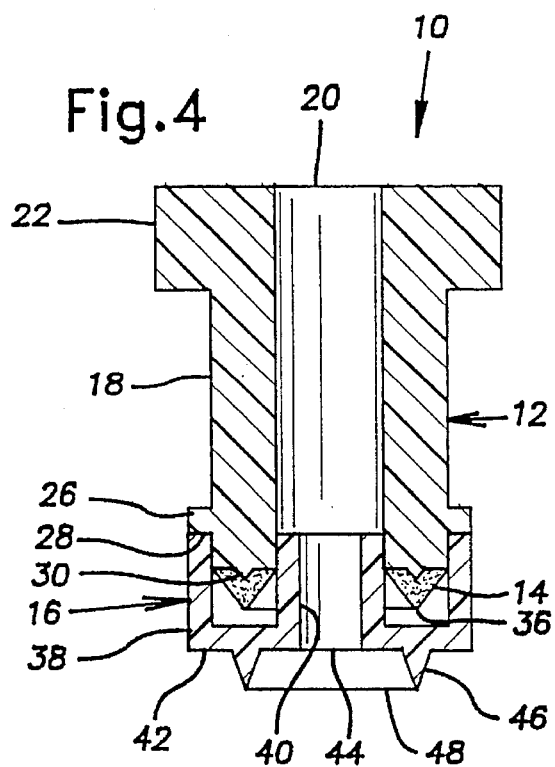
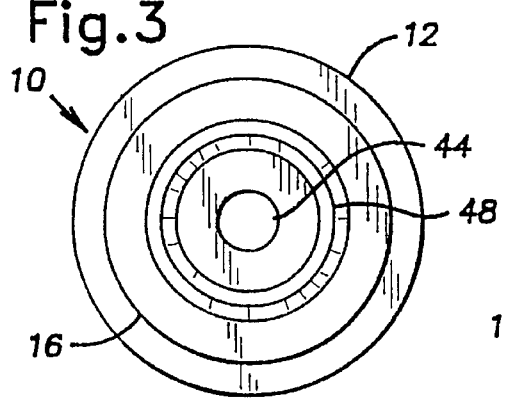
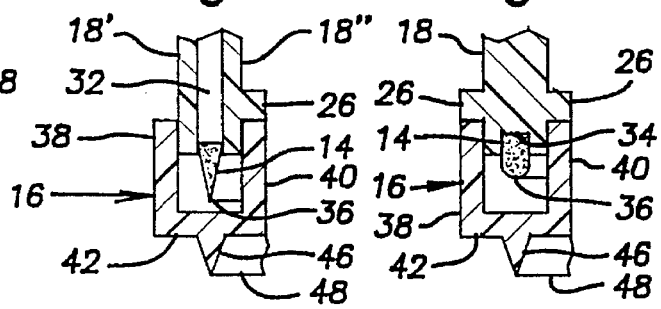

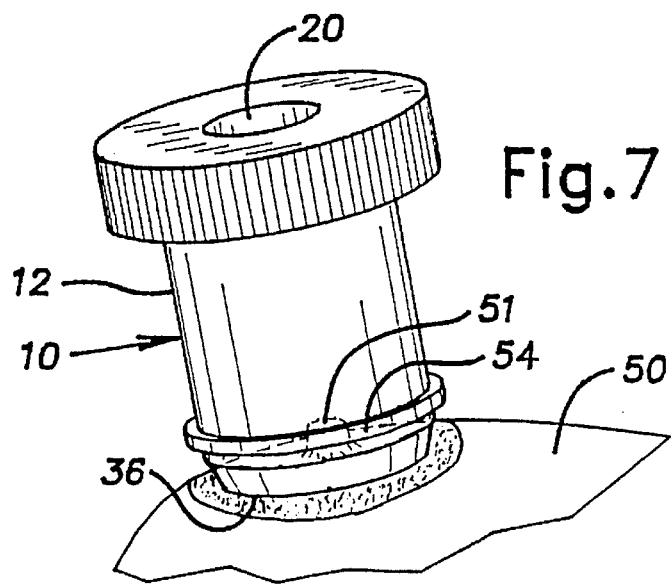
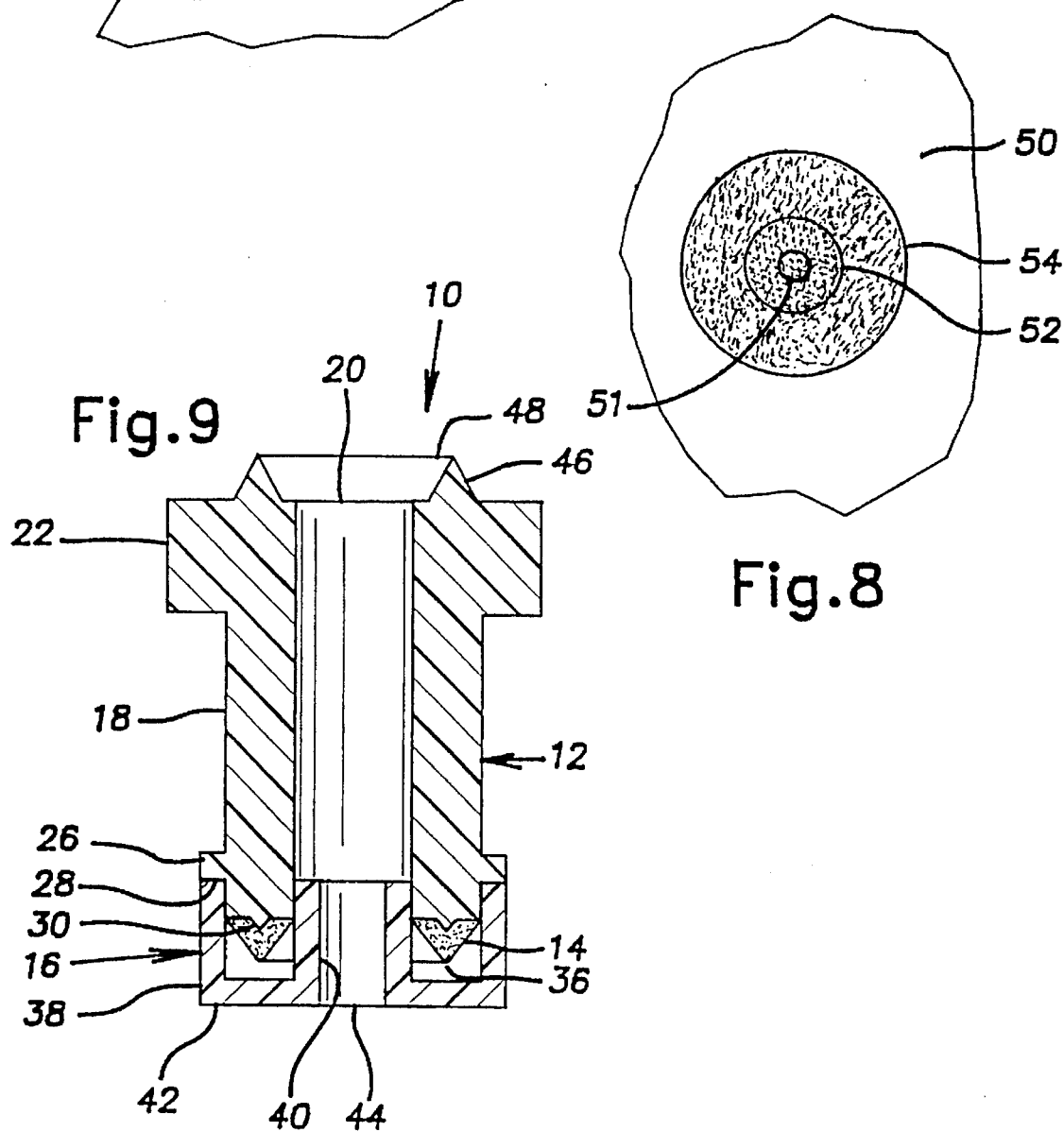

MARKING DEVICE FOR BREAST SURGERY

BACKGROUND OF THE INVENTION

1. Field of the Invention

The present invention relates generally to a device and method for making a circular mark on a breast of a surgical patient, and more particularly, to a device and method which makes a circular imprint to determine an appropriate location for making a circular ink mark.

2. Description of Related Art

In breast surgical procedures such as for example, breast reduction, mastopexy, or nipple reconstruction, it is common to mark the size and shape of the nipple and areola. One approach is to stamp a circular ink mark with an ink marking device. This type of device, however, frequently provides circular ink marks in inappropriate locations such as, for example, eccentrically of the nipple or areola. An uneasy task of removing the ink mark, therefore, is required so that a new ink mark can be properly located. This process may have to be repeated several times.

Another approach has been to use a device with a thin circular edge which when pressed against the skin of the patient's breast creates a circular reddened mark. For example, see U.S. Pat. No. 4,892,096 the disclosure of which is expressly incorporated herein in its entirety. This type of device, however, can provide circular reddened marks in inappropriate locations such as, for example, eccentrically of the nipple. The surgeon must wait, therefore, until the mark disappears before making a new circular reddened mark to avoid multiple reddened marks which cannot easily be distinguished one from another. This process may have to be repeated several times. Additionally, some surgeons may prefer the greater visibility of a circular ink mark.

Accordingly, there is a need in the art for a marking device for use in breast surgery that is easy to use, disposable, lightweight, inexpensive to produce, time conserving, and provides a distinguishable non-permanent circular mark at an appropriate location on the breast.

SUMMARY OF THE INVENTION

The present invention provides a marking device for breast surgery which overcomes the above-described problems of the related devices. The marking device includes a body, a circular marking pad disposed on a front end of the body and adapted to hold ink, and a projection extending from the device and defining a circular, pointed marking edge having substantially the same diameter as the marking pad. In a preferred embodiment, the marking device also includes a removable cap covering the marking pad and secured to the body with the projection disposed on a front face of the cap.

According to the invention, a method of marking a breast for surgery includes the step of making a circular imprint on the breast so as to discolor flesh thereof. Once an imprint is made, a circle of ink is stamped substantially where the circular imprint was made. In a preferred embodiment, the method also includes the steps of examining a location of the circular imprint before stamping the circle of ink and determining whether the location of the circular imprint is accurate. If the location is not accurate, than the circular imprint is rubbed to reduce the discoloration and another circular imprint is made prior to stamping the circle of ink.

BRIEF DESCRIPTION OF THE DRAWINGS

These and further features of the present invention will be apparent with reference to the following description and drawings, wherein:

FIG. 1 is a top plan view of a breast marking device in accordance with the present invention;

FIG. 2. is an elevational view of the breast marking device of FIG. 1;

FIG. 3 is a bottom plan view of the breast marking device of FIG. 1;

FIG. 4 is an elevation view, in cross-section, of the breast marking device of FIG. 1, taken along line 4—4 of FIG. 2;

FIG. 5 is an elevational fragmented view, in cross-section, in the area of a marking pad of a variation of the breast marking device;

FIG. 6 is an elevational fragmented view, in cross-section, in the area of the marking pad of another variation of the breast marking device;

FIG. 7 is a perspective illustration of the breast marking device in an operative position;

FIG. 8 is a plan view of an areola of a patient's breast with a circular ink mark created by the breast marking device; and FIG. 9 is an elevation view, in cross-section, of a yet another variation of the breast marking device.

DETAILED DESCRIPTION OF THE PREFERRED EMBODIMENT

FIGS. 1–4 illustrate a marking device 10 for breast surgery in accordance with the present invention. The marking device 10 includes a body 12, a circular marking pad 14, and a cap 16. The tubularly-shaped body 12 is formed by an annular wall 18 which has a central aperture or opening 20. The annular wall 18 also has an increased diameter portion 22 at a rear end. Preferably, the outer surface of the increased diameter portion 22 has indentations or raised ridges to provide a gripping surface 24 such as, for example, a knurled surface. The wall 18 also has a flange or stop 26 near a front end of the body 12 and extending from an outer surface of the body 12 which forms a forward facing shoulder or engagement surface 28. It is noted that the stop 26 can alternatively extend from an inner surface of the body 12 or from both the outer and inner surfaces of the body 12 as shown in FIGS. 5 and 6 respectively. At the front end of the wall 18 is a triangularly-shaped protrusion 30 extending into the marking pad 14. The body 12 is preferably formed from a plastic such as, for example, polypropylene, polycarbonate, or polystyrene.

The circular marking pad 14 is attached to the front end of the wall 18 where the protrusion 30 provides both increased surface contact and lateral support. It is noted that the marking pad 14 can be attached to the wall 18 in other configurations such as, for example, as shown in FIGS. 5 and 6. As shown in FIG. 5, the front end of the wall 18 can be formed from a pair of annular walls 18', 18" spaced for receiving a base of the marking pad 14 in a space 32 therebetween. As shown in FIG. 6, the front end of the wall 18 can have a recess 34 sized for receiving the base of the marking pad 14.

The circular marking pad 14 is generally annularly-shaped with a generally triangularly-shaped cross section such that it is capable of marking a circle. The base of the marking pad 14 is adjacent the front end of the wall 18 such that a marking end 36 of the marking pad 14 extends away from the body 12. The marking end 36 is concentric with the opening 20 in the base 12. The marking end 36 is preferably a sharp edge, as shown in FIGS. 4 and 5, capable of marking a generally thin-lined circle. It is noted however that the marking end 36 could alternatively be blunt or rounded as shown in FIG. 6. The marking pad preferably marks a circle having a diameter of either 38 mm or 42 mm which are commonly used nipple/areola sizes.

The marking pad 14 is preferably formed of a porous or fibrous material such as, for example, felt so that it is capable of holding non-permanent ink. With the marking pad 14 impregnated with ink, it operates in the same manner as a felt-tipped pen. It is noted, however, that the marking pad 14 could be made of a non-porous material but the marking pad 14 would have to be pressed on an ink pad prior to use.

The cap 16 has a pair of annular walls 38, 40 connected by a base wall 42 to form a generally U-shaped cross-section. The annular walls 38, 40 are sized to frictionally engage the inner and outer surfaces of the annular wall 18 of the body 12 to removably secure the cap 16 to the body 12 and cover the marking pad 14 and prevent the marking pad 34 from drying out. An end of the outer annular wall 38 engages the engagement surface 28 of the stop 26 to limit movement of the cap 16 on the body 12 to space the cap 16 from the marking end 36 of the marking pad 14. The cap 16 also has a central aperture or opening 44 which is substantially concentric with the opening 20 of the body 12.

A generally rigid projection 46 extends from the front end of the cap 16. The projection 46 is generally annularly-shaped with a generally triangularly-shaped cross section to form a circular, pointed, marking edge 48. It is noted that other cross-sections can be utilized to obtain the marking edge 48. The marking edge 48 has a diameter substantially the same size as the marking end 36 of the marking pad 14 and is substantially concentric with the marking end 36 of the marking pad 14. The marking edge 48 is also substantially concentric with the opening 44 of the cap 16. The cap 16 is preferably formed from a plastic such as, for example, polypropylene, polycarbonate, or polystyrene.

A variation of the marking device 10 is shown in FIG. 9 using like numbers for like references. The projection 46 is located at the rear face of the body 12 rather than at the front face of the cap 16. It is noted that the projection 46 can alternatively be in other locations such as, for example, the front face of the body 12.

The marking device 10 is positioned on the breast 50 of a surgical patient in concentric alignment with the breast nipple 51 and/or areola 54 such as, for example, by looking through the opening 20 in the body 12 of the device 10. The marking edge 48 of the marking device 10 is pressed against the skin of the breast 50, and may be twisted, to create a temporary circular skin discoloration imprint, indentation, or groove on the skin of the breast 50. The circular imprint corresponds to the location where a circular ink mark will subsequently be made. The circular imprint is examined to determine whether the location of the circular imprint is accurate. If the location is not accurate, the circular imprint is rubbed to reduce the discoloration and another circular imprint is made. This process is easily repeated without the need to remove ink.

When the location of the circular imprint is accurate, the cap 16 is removed and the marking device 10 is positioned concentric with the final circular imprint, as shown in FIG. 8. The marking end 36 of the marking pad 14 is pressed against the skin of the breast 50 to create a circular ink mark 52 on the skin of the breast 50 as shown in FIG. 8. The circular ink mark 52 is thereby located at the final circular imprint, that is, at the desired accurate location. The marking device 10 may thereafter be disposed.

Although particular embodiments of the invention have been described in detail, it will be understood that the invention is not limited correspondingly in scope, but includes all changes and modifications coming within the spirit and terms of the claims appended hereto.

What is claimed is:

1. A marking device comprising:

a body;

a circular marking pad disposed on a front end of said body and adapted to hold ink; and a projection extending from the device and defining a circular, pointed marking edge having substantially the same diameter as the marking pad.

2. The marking device according to claim 1, wherein said marking edge is substantially concentric with said marking pad.

3. The marking device according to claim 2, wherein said marking edge is disposed on a rear end of said body.

4. The marking device according to claim 1, further comprising ink held by said marking pad.

5. The marking device according to claim 1, wherein said marking pad is porous.

6. The marking device according to claim 5, wherein said marking pad is felt.

7. The marking device according to claim 5, further comprising ink held in said marking pad.

8. The marking device according to claim 1, wherein said body is annular.

9. The marking device according to claim 1, further comprising a removable cap covering said marking pad and secured to said body.

10. The marking device according to claim 9, wherein said body and said cap are annular.

11. The marking device according to claim 10, wherein said cap has a pair of annular walls frictionally engaging said body to space said cap from said marking pad.

12. The marking device according to claim 9, further comprising a stop adapted to space said cap from said marking pad.

13. The marking device according to claim 12, wherein said stop is disposed on said body and is adapted to limit movement of said cap on said body.

14. The marking device according to claim 13, wherein said cap has a pair of annular walls frictionally engaging said body and said stop to space said cap from said marking pad.

15. The marking device according to claim 9, wherein said projection is disposed on a front face of said cap.

16. The marking device according to claim 15, wherein said marking edge is substantially concentric with said marking pad.

17. A breast marking device comprising:

an annular body;

a circular felt pad disposed on a front end of said body;

ink held in the pad;

a removable annular cap covering said felt pad and secured to said body, said cap having a pair of annular walls frictionally engaging said body; and a projection extending from a front face of the cap and defining a circular, pointed marking edge substantially concentric with said felt pad and having substantially the same diameter as said felt pad.

18. The breast marking device according to claim 17, further comprising a stop on said body adapted to limit movement of said cap on said body, said cap engaging said stop to space said cap from said felt pad.

* * * * *